United States Patent [19]
Bayly et al.

[11] Patent Number: 5,994,379
[45] Date of Patent: Nov. 30, 1999

[54] BISARYL COX-2 INHIBITING COMPOUNDS, COMPOSITIONS AND METHODS OF USE

[75] Inventors: Christopher I. Bayly, Pointe Claire; Cameron Black, Springdale Pointe Claire; Nathalie Ouimet, Ile Perrot; David Percival, Montreal West; Serge Leger, Dollard Des Ormeaux; Marc Ouellet, Lachine, all of Canada

[73] Assignee: Merck Frosst Canada, Inc., Kirkland, Canada

[21] Appl. No.: 09/246,925

[22] Filed: Feb. 9, 1999

Related U.S. Application Data

[60] Provisional application No. 60/074,627, Feb. 13, 1998.

[51] Int. Cl.$^6$ .......... A61K 31/425; A61K 31/42; A61K 31/38; A61K 31/34; A61K 31/215; A61K 31/19; C07C 321/28; C07C 59/64; C07C 57/42; C07C 57/38; C07D 277/64; C07D 263/56; C07D 235/06; C07D 209/44; C07D 209/18

[52] U.S. Cl. .......... 514/367; 514/249; 514/277; 514/350; 514/375; 514/400; 514/415; 514/416; 514/443; 514/469; 514/532; 514/570; 514/247; 544/349; 544/224; 546/121; 546/301; 546/302; 546/342; 548/217; 548/310.1; 548/470; 548/510; 549/58; 549/454; 560/9; 560/59; 560/102; 562/426; 562/469; 562/492

[58] Field of Search .......... 560/9, 59, 102; 562/426, 469, 492; 548/510, 180, 217, 310.1, 470; 549/58, 454; 514/367, 375, 400, 415, 416, 443, 469

[56] References Cited

U.S. PATENT DOCUMENTS 3,755,427  8/1973  Adams et al.

OTHER PUBLICATIONS

Futaki, Nobuko, et. al.Gen Pharmac. vol. 24, No. 1 pp. 105–110 (1993).

Smith, William L. et. al., The Journal of Biological Chemistry, vol. 271, No. 52 pp. 33157–33160 (1996).

Daniel Picot, et al., Nautre, vol. 367 pp. 243–249, 215–216 (1994).

Gans, Kathleen, et al., The Journal of Pharmacology and Experimental Therapeutic, vol. 254, No. 1 pp. 180–187, (1990).

Copeland, Robert A., et al., Proc. Nutl. Acad. Sci. USA, vol. 91, pp. 11202–11206, (1994).

Ouellet, Marc, et al., Biochem. J. vol. 306, pp. 247–251, (1995).

Vane, J. R. et. al., Inflamm Res 44: 1–10, (1995).

Kurumbail, Ravi G. et. al., Nature, vol. 384, pp. 644–648 (1996).

Luong, Christine N., et al., Nature Structural Biology, vol. 3, pp. 927–933 (1996).

*Primary Examiner*—Michael G. Ambrose
*Attorney, Agent, or Firm*—Richard C. Billups; David L. Rose

[57] ABSTRACT

The present invention relates to inhibitors of COX-2, compositions which contain such compounds and methods of use. The compounds are represented by formula I:

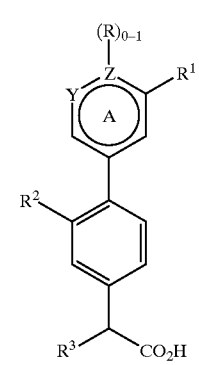

and include pharmaceutically acceptable salts and esters thereof.

16 Claims, No Drawings

BISARYL COX-2 INHIBITING COMPOUNDS, COMPOSITIONS AND METHODS OF USE

CROSS REFERENCE TO RELATED APPLICATIONS

This application claims the benefit of U.S. provisional application Ser. No. 60/074,627, filed on Feb. 13, 1998.

The present invention relates to compounds which are inhibitors of COX-2, compositions which contain such compounds and methods of use.

BACKGROUND OF THE INVENTION

Cyclooxygenase (COX), also known as prostaglandin H synthase, is an enzyme implicated in the mediation of pain, fever and inflammation. It catalyzes the oxidative conversion of arachidonic acid into prostaglandin $H_2$, a key intermediate in the biosynthetic pathway of prostaglandins, prostacyclins and thromboxanes, which in turn mediate a variety of physiological effects both beneficial and pathological. Recently it was discovered that two COX isoforms exist: COX-1, expressed constitutively in many tissues, and COX-2, an induced isoform having elevated levels of expression in inflamed tissues. COX-1 is thought to be involved in ongoing "housekeeping" functions, for example gastric cytoprotection, while COX-2 is implicated in the pathological effects mentioned above.

Current cyclooxygenase inhibitors such as aspirin, ibuprofen and indomethacin, used as non-steroidal anti-inflammatory drugs (NSAIDs), inhibit both COX-1 and COX-2 and have associated side effects, such as gastrotoxicity, which may be manifested as ulcer formation. COX-2 selective inhibitors act as effective NSAIDs without substantial gastrotoxic side effects.

The first published COX X-ray crystal structure was of sheep COX-1 complexed with flurbiprofen, a non-selective NSAID. Subsequently, the crystal structure of human COX-2 complexed with an indomethacin analog was discovered. Other COX-2 crystal structures have recently been determined.

SUMMARY OF THE INVENTION

The present invention relates to a compound represented by formula I:

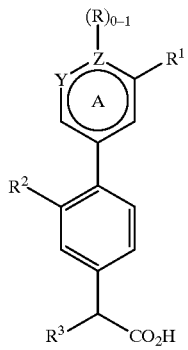

or a pharmaceutically acceptable salt, ester or tautomer thereof, wherein:

Z is C or N;
when Z is N, R represents H or is absent, or is taken in conjunction with $R^1$ as described below:

when Z is C, R represents H and $R^1$ is a moiety which has the following characteristics:
(a) it is a linear chain of 3-4 atoms containing 0–2 double bonds, which can adopt an energetically stable transoid configuration and if a double bond is present, the bond is in the trans configuration;
(b) it is lipophilic except for the atom bonded directly to ring A, which is either lipophilic or non-lipophilic; and
(c) there exists an energetically stable configuration planar with ring A to within about 15 degrees, or R and $R^1$ are taken in combination and represent a 5- or 6-membered aromatic or non-aromatic ring B fused to ring A, said ring B containing 0–3 heteroatoms selected from O, S and N,
said ring B being lipophilic except for the atoms attached directly to ring A, which are lipophilic or non-lipophilic, and said ring B having available an energetically stable configuration planar with ring A to within about 15 degrees;
said ring B further being substituted with 1 $R^a$ group selected from the group consisting of: $C_{1-2}$ alkyl, $-OC_{1-2}$ alkyl, $-NHC_{1-2}$ alkyl, $-N(C_{1-2}$ alkyl$)_2$, $-C(O)C_{1-2}$ alkyl, $-S-C_{1-2}$ alkyl and $-C(S)C_{1-2}$ alkyl;

Y represents N, CH or C—$OC_{1-3}$ alkyl, and when Z is N, Y can also represent a carbonyl group;

$R^2$ represents H, Br, Cl or F, and $R^3$ represents H or $CH_3$.

Pharmaceutical compositions and methods of treatment are also included.

DETAILED DESCRIPTION

The present invention is described using the following definitions unless otherwise indicated.

The term "energetically stable transoid configuration" means that torsion angles describing the bonds connecting the non-hydrogen atoms, including the bond connecting the substituent to the ring, possess a local potential energy minimum between 165°–195°. Potential energy minimum applies here to in vacuo minimizations using a conventional small-molecule force field such as MMFF (T. A. Halgren, J Comput. Chem. 17, pp. 490–519 (1996) and references therein).

The term "lipophilic substituent" means a substituent having low polarity such that a compound principally composed of such substituents would have an octanol-water partition coefficient of log P$\geq$0.8.

The term "linear chain of 3-4 atoms containing 0–2 double bonds" is used in its conventional sense, and includes alkyl groups which are linear or substantially linear, having 3-4 carbon atoms. Thus, propyl, and butyl are included, as are chains containing 2-3 carbon atoms which are bound to the phenyl ring through a heteroatom. Alkenyl and alkynyl groups are also included.

Alkenyl refers to 2–4 membered carbon chains, having 1-2 double bonds as appropriate. If the alkenyl group has 2 or 3 carbon atoms, it may be linked to ring A via a heteroatom. If two double bonds are present, they are conjugated. The double bond or bonds are in the trans configuration.

Alkynyl refers to a hydrocarbon radical straight, branched or cyclic, containing from 2 to 4 carbon atoms and at least one carbon to carbon triple bond. Preferred alkynyl groups include ethynyl, propynyl and butynyl.

Heteroatom means O, S or N, selected on an independent basis.

Cyclic structures are included, such as in the following structures:

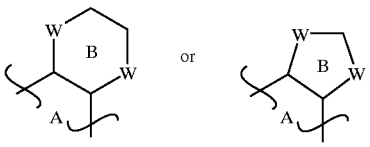

where W represents C or a heteroatom, and ring B can assume a configuration that is planar or substantially planar (to within about 15 degrees) with ring A.

The following abbreviations have the indicated meanings:
AA=arachidonic acid
Ac=acetyl
AIBN=2.2-azobisisobutyronitrile
Bn=benzyl
CSA=camphor sulfonic acid
DMAP=4-(dimethylamino)pyridine
DMF=N,N-dimethylformamide
DMSO=dimethyl sulfoxide
$Et_3N$=triethylamine
HBSS=Hanks balanced salt solution
HEPES=N-[2-Hydroxyethyl]piperazine-$N^1$-[2-ethanesulfonic acid]
HWB=human whole blood
KHMDS=potassium hexamethyldisilazane
LDA=lithium diisopropylamide
LPS=lipopolysaccharide
MMPP=magnesium monoperoxyphthalate
Ms=methanesulfonyl=mesyl
MsO=methanesulfonate=mesylate
NSAID=non-steroidal anti-inflammatory drug
OXONE™=$2KHSO_5$-$KHSO_4$-$K_2SO_4$
PCC=pyridinium chlorochromate
PDC=pyridinium dichromate
Ph=phenyl
r.t.=room temperature
rac.=racemic
Tf=trifluoromethanesulfonyl=triflyl
TfO=trifluoromethanesulfonate=triflate
TFOH=trifluoromethane sulfonic acid
THF=tetrahydrofuran
TLC=thin layer chromatography
Ts=p-toluenesulfonyl=tosyl
TsO=p-toluenesulfonate=tosylate
$SO_2Me$=methyl sulfone
$SO_2NH_2$=sulfonamide
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl The term "alkyl" in general means linear, branched or cyclic structures and combinations thereof, containing the indicated number of carbon atoms. Examples of alkyl groups include methyl, ethyl, cyclopropyl, isopropyl, butyl, t-butyl, pentyl, hexyl, cyclohexyl, heptyl, pentadecyl, eicosyl, 3,7-diethyl-2,2-dimethyl-4-propylnonyl, and the like.

"Alkoxy" means alkoxy groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like.

"Alkylthio" means alkylthio groups of the indicated number of carbon atoms of a straight, branched or cyclic configuration. Examples of alkylthio groups include methylthio, propylthio, isopropylthio, cycloheptylthio, etc. By way of illustration, the propylthio group signifies —$SCH_2CH_2CH_3$.

Halogen includes F, Cl, Br, and I.

A preferred aspect of the invention relates to compounds represented by formula I:

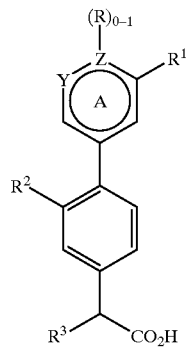

I as well as pharmaceutically acceptable salts, esters and tautomers thereof, wherein:

Z is C or N;
when Z is N, R represents H or is absent, or is taken in conjunction with $R^1$ as described below:
when Z is C, R represents H and $R^1$ represents a member selected from the group consisting of:
—$C_{3-4}$ alkenyl, —$C_{3-4}$ alkynyl, —X—$C_{2-3}$ alkynyl, —X—$C_{2-3}$ alkyl and —X—$C_{2-3}$ alkenyl,
wherein X represents O, S or NH;
or R and $R^1$ are taken in combination and together represent a 5- or 6-membered aromatic or non-aromatic ring B fused to ring A containing 0–3 heteroatoms selected from O, S and N;
said ring B further being substituted with 1 Ra group selected from the group consisting of: $C_{1-2}$ alkyl, —$OC_{1-2}$ alkyl, —$NHC_{1-2}$ alkyl, —$N(C_{1-2}$ alkyl$)_2$, —$C(O)C_{1-2}$ alkyl, —S—$C_{1-2}$ alkyl and —$C(S)C_{1-2}$ alkyl;
Y represents N, CH or C—$OC_{1-3}$ alkyl, and when Z is N, Y can also represent a carbonyl group;
$R^2$ represents H, Br, Cl or F, and
$R^3$ represents H or $CH_3$.

Another aspect of the invention that is of interest relates to compounds of formula I wherein R represents H and $R^1$ represents a member selected from the group consisting of:

—X-ethyl, —X-propyl, —X-vinyl, —X—CH=CHCH$_3$
—X—CH$_2$CH=CH$_2$, —CH=CHCH=CH$_2$,
—C≡CCH$_3$ and —C≡CCH$_2$CH$_3$,
wherein X represents O, S or NH.

Another aspect of the invention relates to compounds of formula I wherein R and $R^1$ are taken in combination and together represent a 5- or 6-membered aromatic or non-aromatic ring B fused to ring A of the formula:

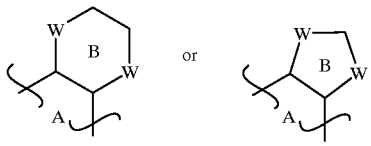

wherein each W independently represents C, O, S or N;
said ring B further being substituted with 1 $R^a$ group selected from the group consisting of: $C_{1-2}$ alkyl, —O$C_{1-2}$ alkyl, —NH$C_{1-2}$ alkyl, —N($C_{1-2}$ alkyl)$_2$, —C(O)$C_{1-2}$ alkyl, —S—$C_{1-2}$ alkyl and —C(S)$C_{1-2}$ alkyl;

Y represents N, CH or C—O$C_{1-3}$ alkyl, and
$R^2$ represents H, Br, Cl or F.

Examples of species which fall within the invention include the following:

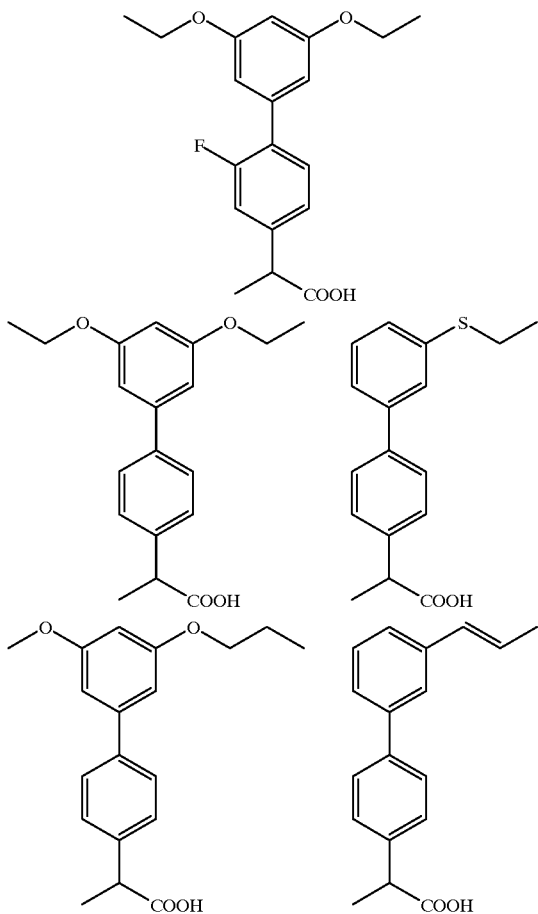

-continued

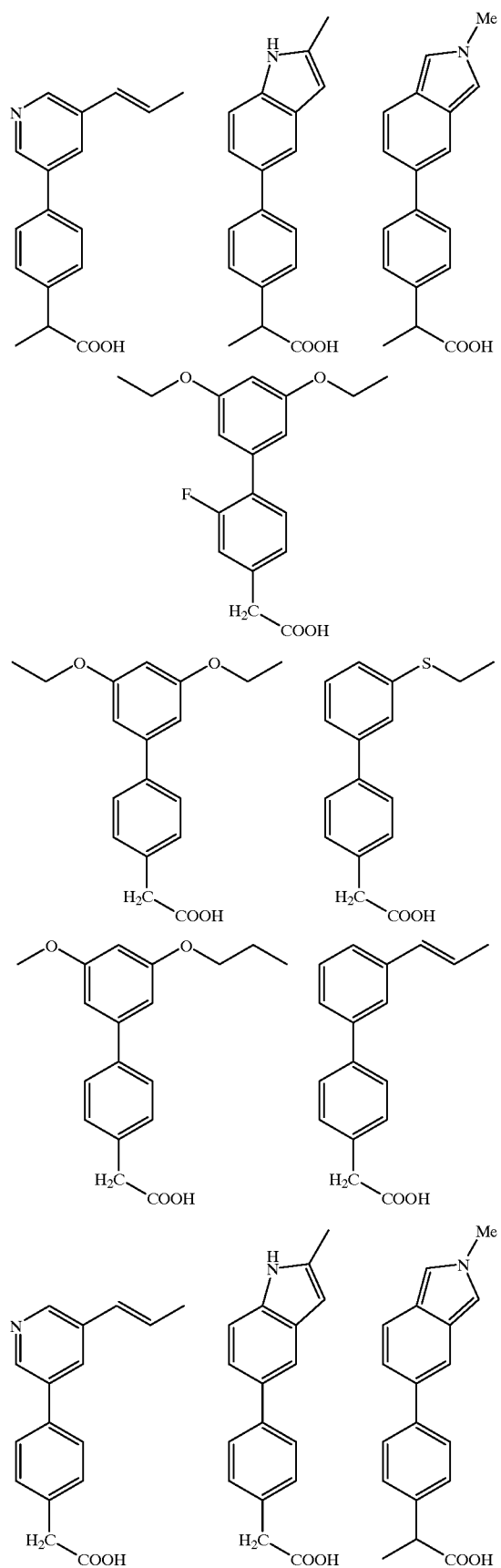

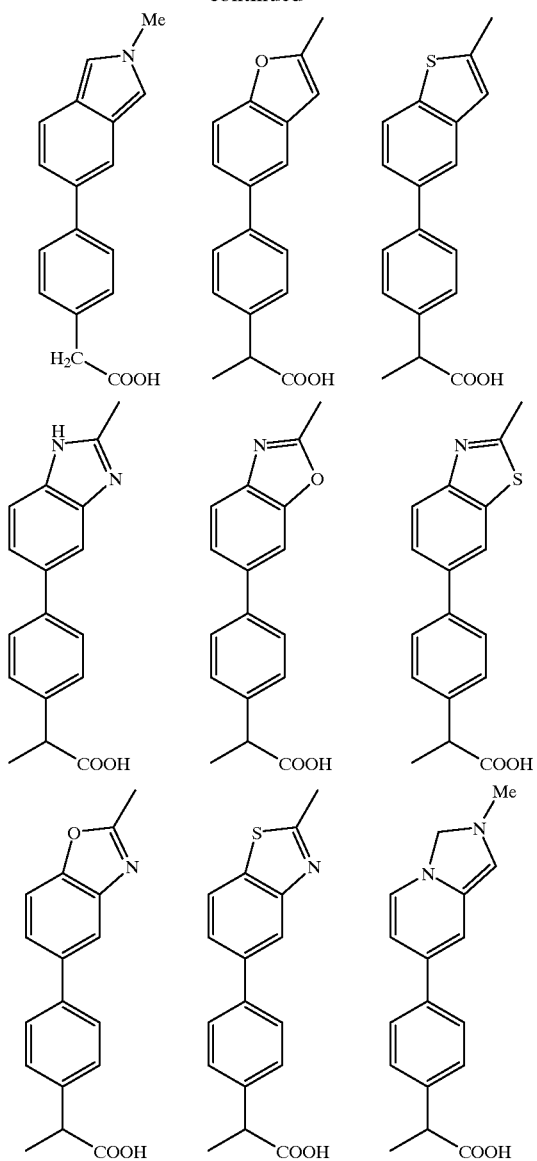

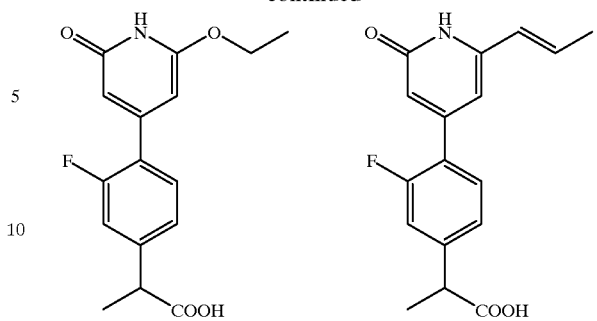

Salts, esters of the carboxylic acid moiety and tautomers are also included.

Tautomer as used herein refers to the keto-enol forms of the compounds of the invention, where such forms are possible. One example of a tautomer is as follows:

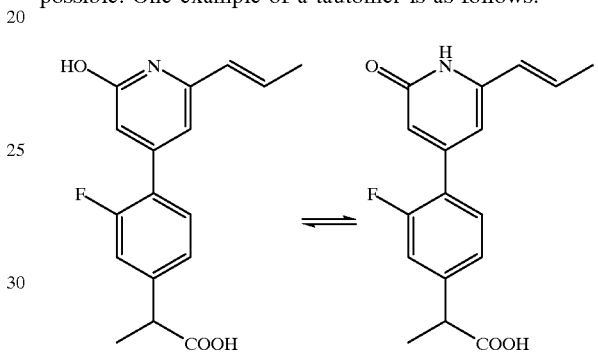

All such tautomers are included in the present invention.

In another embodiment, the invention described herein encompasses a pharmaceutical composition comprising a compound of formula I or a salt or ester thereof in combination with a pharmaceutically acceptable carrier.

In another embodiment, the invention described herein encompasses a method of treating or preventing a COX-2 mediated disease in a mammalian patient in need of such treatment, comprising administering to said patient a compound of formula I patient in an amount which is effective for treating or preventing said COX-2 mediated disease. As used herein, "COX-2 mediated diseases" include the diseases and conditions which are mentioned herein.

The compounds described herein contain one or more asymmetric centers and thus give rise to diastereomers and optical isomers. The present invention includes all such possible isomers, in pure form as well as in racemic mixture, and pharmaceutically acceptable salts and esters thereof.

Salts of the compounds of formula I are prepared from, e.g., pharmaceutically acceptable inorganic and organic bases. Representative examples of suitable salts include ammonium, alkylammonium, dialkylammonium, trialkylammonium, tetraalkylammonium, sodium, potassium, calcium and magnesium salts. In these salt forms, the carboxylate group is in its anionic form in association with the pharmaceutically acceptable cation. Preferably the cation is sodium, potassium calcium or magnesium. More preferred are sodium and potassium. Most preferred is sodium.

Ester forms of the compounds are also included in the present invention. In this aspect of the invention, the carboxylic acid is esterified using a conventional esterifying agent. Examples include pharmaceutically acceptable aliphatic alcohols and diols. Preferred are methyl and ethyl esters.

Salts and esters of the carboxylic acid moiety are also included.

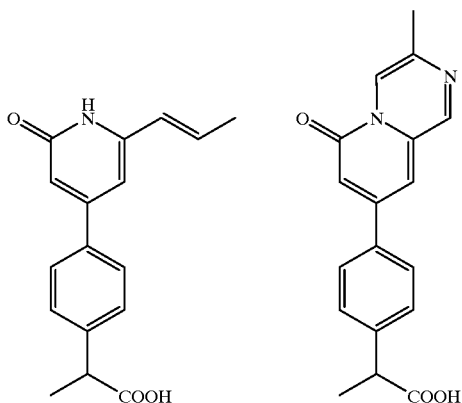

The methods of treatment described herein apply equally to pharmaceutically acceptable salts, esters and tautomers of the compounds of formula I.

The compounds are useful for the relief of pain, fever and inflammation of a variety of conditions including, e.g., rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures.

In addition, by inhibiting COX-2, the compounds inhibit cellular neoplastic transformations and metastic tumour growth, and hence can be used in the treatment of cancer.

In addition, the compounds are also of use in the treatment and/or prevention of cyclooxygenase-mediated proliferative disorders, such as diabetic retinopathy and tumour angiogenesis.

In addition, the compounds of the present invention are useful in the treatment or prevention of autoimmune diseases, such as diabetes, including type I and type II diabetes, lupus erythematosus and other lupus-like syndromes, Graves' disease, rheumatoid arthritis, osteoarthritis, irritable bowel syndrome, Crohn's disease and other autoimmune diseases.

In addition, the compounds inhibit prostanoid-induced smooth muscle contraction by preventing the synthesis of contractile prostanoids and hence are of use in the treatment of dysmenorrhea, premature labour, asthma and eosinophil related disorders. The compounds are also of use in the treatment of Alzheimer's disease, for decreasing bone loss particularly in postmenopausal women (i.e. treatment of osteoporosis) and for the treatment of glaucoma.

By virtue of high inhibitory activity against COX-2 and/or specificity for COX-2 over COX-1, the compounds are useful as an alternative to non-COX-2 selective NSAIDs, particularly where such non-steroidal antiinflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anaemia such as hypoprothrombinemia, haemophilia or other bleeding problems; kidney disease; those prior to surgery or taking anticoagulants.

For the treatment of any of these cyclooxygenase mediated diseases, a compound of formula I may be administered orally, topically, parenterally, by inhalation, spray, rectally or intravaginally in formulations containing pharmaceutically acceptable carriers.

The term parenteral as used herein includes subcutaneous injections, intravenous, intramuscular, intrasisternal injection or infusion techniques. In addition to the treatment of warm-blooded animals such as mice, rats, horses, cattle sheep, dogs, cats, etc., the compounds of the invention are useful in the treatment of humans.

The pharmaceutical compositions described herein may include one or more other active ingredients.

The composition may be in a form suitable for oral use, for example, tablets, troches, lozenges, aqueous or oily suspensions, dispersible powders or granules, emulsions, hard or soft capsules, solutions, syrups and elixirs. Compositions intended for oral use may be prepared according to any method known to the art for the manufacture of pharmaceutical compositions and typically such compositions contain one or more agents selected from the group consisting of sweetening agents, flavouring agents, colouring agents and preservatives in order to provide pharmaceutically elegant and palatable preparations. These excipients may be for example, diluents such as lactose, calcium carbonate, sodium carbonate, calcium phosphate or sodium phosphate; granulating and disintegrating agents, for example, corn starch or alginic acid; binding agents, for example starch, gelatin or acacia, and lubricating agents, for example, magnesium stearate, stearic acid or talc.

The tablets may be uncoated or they may be coated. Coating can be included to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166, 452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or miscible solvents such as propylene glycol, PEGs and ethanol, or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, tragacanth and acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain demulcents, preservatives, flavourants and colouring agents.

The pharmaceutical compositions may be in the form of a sterile injectable aqueous or oleagenous suspension. This suspension may be formulated according to the known art using those suitable dispersing or wetting agents and suspending agents which have been mentioned above.

Injectable compositions are typically in the form of sterile solutions or suspensions, which include the active ingredient in a parenterally-acceptable diluent. Among these are sterile water, dextrose 5% in water (D5W), Ringer's solution and isotonic saline, as well as mixtures thereof Cosolvents such as ethanol, propylene glycol or polyethylene glycols may also be used. Sterile, injectable oil is occasionally employed as a solvent or suspending medium in intramuscular preparations. A representative example is peanut oil. In addition, fatty acids such as oleic acid, preservatives, buffers and local anesthetics find use in the preparation of intramuscular injectables.

Compound I may also be administered rectally or intravaginally as suppositories. These can be prepared by mixing the drug with a suitable non-irritating excipient which is solid at ordinary room temperature but molten at normal or elevated body temperature. Examples of such materials include cocoa butter and polyethylene glycols.

For topical use, creams, ointments, gels, solutions, suspensions and the like containing the compound are employed. (For purposes of this application, topical application includes mouth washes and gargles, as well as transdermal applications.) Topical formulations are comprised of a pharmaceutical carrier, which may include, e.g., cosolvents, emulsifiers, penetration enhancers, preservatives or emollients.

Dosage levels on the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The active ingredient is combined with the carrier to produce the dosage form. The amount varies depending upon the host treated, the particular mode of administration and other factors. For example, a formulation intended for oral administration may contain from as low as about 0.1 mg to as high as about 5 g of active agent per dose, compounded with an appropriate and convenient amount of carrier material which may vary from about 6 to about 95 percent of the total composition. Dosages generally range from as low as about 0.1 mg to as high as about 1500 mg of the active ingredient, more particularly about 25 mg to about 1000 mg.

It is understood that the dosage for any particular patient depends upon a variety of factors, including age, body weight, general health, sex, diet, time of administration, route of administration, rate of excretion, drug combination and the severity of the particular disease undergoing therapy. For these reasons, dosing is left to the discretion of the skilled clinician.

Compounds of formula I are also useful as substitutes for conventional NSAIDs in preparations wherein they are presently co-administered with other agents or ingredients. Thus, the invention encompasses pharmaceutical compositions as defined above comprising a compound of formula I and one or more other active ingredients, such as another pain reliever, e.g., acetaminophen; a potentiator, e.g., caffeine; an $H_2$-antagonist, e.g., famotidine; an antacid, e.g., aluminum or magnesium hydroxide; an antiflatulent, e.g., simethicone; a decongestant, e.g., phenylephrine, phenylpropanolamine, pseudophedrine, oxymetazoline, ephinephrine, naphazoline, xylometazoline, propylhexedrine or levo-desoxyephedrine; an antiitussive, e.g., codeine, hydrocodone and dextramethorphan; a prostaglandin, e.g., misoprostol, enprostil, rioprostil, ornoprostol or rosaprostol: a diuretic, e.g., hydrochlorothiazide; a sedating or non-sedating antihistamine, diphenhydramine or loratidine and other active compounds.

In addition, the invention encompasses a method of treating cyclooxygenase mediated diseases comprising: administering to a patient in need of such treatment an effective amount of a compound of formula I, optionally co-administered with one or more of such ingredients as listed immediately above.

The compounds can be synthesized in accordance with the following general reaction scheme.

SCHEME I

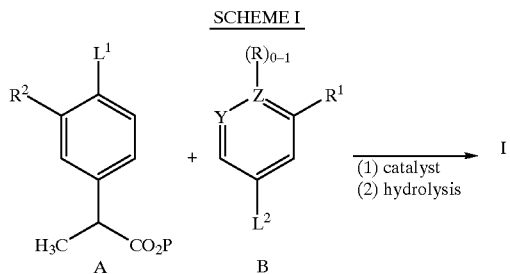

Generally, intermediates A and B are prepared using routine skill or are commercially available, or are described in the literature. These intermediates are reacted in the presence of a transition metal catalyst. The ester can then be hydrolized using base, e.g., NaOH or LiOH to provide a carboxylic acid of formula I.

Typically one of $L^1$ and $L^2$ is a Br, I or OTf, and the other represents a metal containing moiety, such as Zn, Mg, B or Sn. P represents H or a carboxylate protecting group.

Alternatively the group $R^1$ can be added after the reaction of A and B. A leaving group, e.g., Br, at the meta position the diphenyl precursor is then reacted with a side chain precursor under transition metal catalysis. The ester can then be hydrolized to provide the carboxylic acid as previously described.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, N.Y. (1991).

Conventional protecting groups consist of groups which are used to protectively block the carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include C1–6 alkyl, allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

With respect to the synthesis of the compounds described in the examples, each R group is specific to the drawing appearing in the example, and is not intended to be consistent with the generic description of the compounds of the invention. The starting materials can be obtained as described in the examples, or synthesized using routine skill.

$^1$H NMR spectra were recorded on a Bruker AMX-400 or AMX-300 spectrometer. Chemical shifts are reported in ppm from tetramethylsilane with the solvent resonance as the internal standard ($d_6$-acetone: δ 2.04). Low resolution APCI mass spectra were obtained on a Sciex API 100 mass spectrometer. FAB mass spectra and high resolution mass spectra were obtained from the McGill University Biomedical Mass Spectrometry Unit. Combustion analyses were performed at the Department of Chemistry, Université de Montreal.

EXAMPLE 1

2-(4-(3,5-DIETHOXYPHENYL)-3-FLUOROPHENYL) PROPIONIC ACID (4)

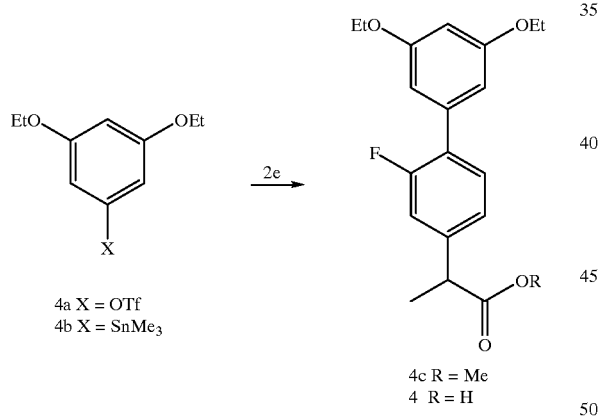

3,5-Diethoxyphenyl trifluoromethanesulfonate (4a)

To a solution of 3–5,diethoxyphenol (580 mg, 3.1 mmol) and diisopropylethylamine (1.0 mL, 5.7 mmol) in $CH_2Cl_2$ (15 mL) at −78° C. was added dropwise triflic anhydride (822 μL, 4.9 mmol). The solution was stirred while warming to room temperature over 2h and water was added. The product was extracted twice using $CH_2Cl_2$, the combined organic layers were washed with brine and dried over $MgSO_4$.

Purification by flash chromatography (33% to 40% EtOAc/hexanes) provided 960 mg of the title compound.

$^1$H NMR (acetone $d_6$) δ 6.53 (m, 3H), 4.08 (m, 4H), 1.38 (m, 6H).

3,5-Diethophenyl trimethyl tin (4b)

This compound was prepared from 4a following the procedure described for example 3b.

Methyl 2-(4-(3,5-diethoxyphenyl)-3-fluorophenyl) propanoate (4c)

This compound was prepared from 4b following the procedure described for example 3c. Purification by flash chromatography (4:2:0.5 hexanes:$CH_2Cl_2$:EtOAc) provided 200 mg of the title compound.

$^1$H NMR (acetone $d_6$) δ 7.47 (t, 1H), 7.18 (t, 2H), 6.66 (m, 2H), 6.49 (m, 1H), 4.07 (q, 4H), 3.85 (q, 1H), 3.65 (s, 3H), 1.48 (d, 3H), 1.35 (t, 6H).

2-(3',5'-Diethoxy-2-fluoro-biphenyl-4-yl)-propionic acid (4)

The hydrolysis of 4c followed the procedure described in the preparation of compound 2. Purification by flash chromatography (20% EtOAc/toluene+2% AcOH) provided 350 mg of the title compound.

$^1$H NMR (acetone $d_6$) δ 7.48 (t, 1H), 7.22 (t, 2H), 6.66 (m, 2H), 6.49 (m, 1H), 4.07 (q, 4H), 3.85 (q, 1H), 1.50 (d, 3H), 1.38 (t, 6H). MS (FAB+) m/z 377 (M+Na), 287.

EXAMPLE 2

2-[4-(3,5-DIETHOXYPHENYL)PHENYL] PROPIONIC ACID (8)

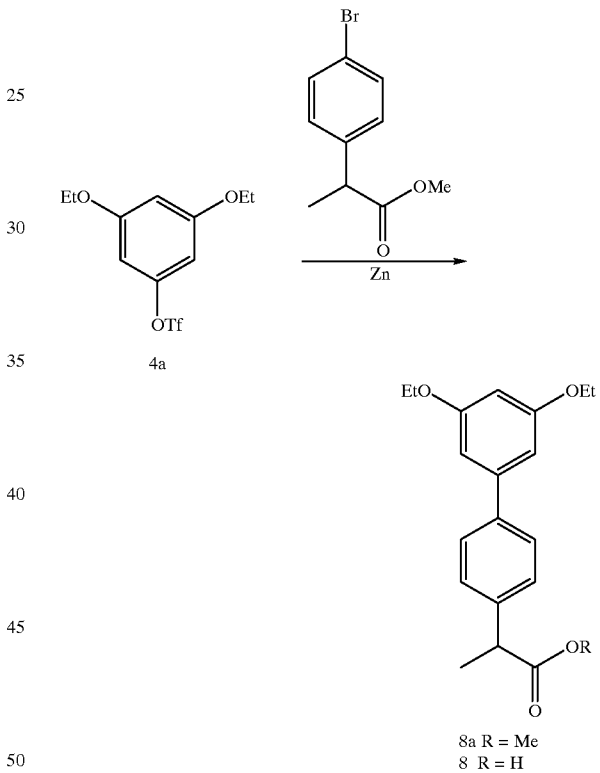

Methyl 2-[4-(3,5-diethoxyhenyl)phenyl]propanoate (8a)

This compound was prepared from 4a and methyl 2-(4-bromophenyl)propanoate following the procedure described for example 5b. Purification by flash chromatography (20% $Et_2O$/hexanes) provided 70 mg of the title compound.

$^1$H NMR (acetone $d_6$) δ 7.57 (d, 2H), 7.35 (d, 2H), 6.73 (s, 2H), 6.45 (s, 1H), 4.08 (m, 4H), 3.82 (m, 1H), 3.63 (s, 3H), 1.48 (d, 3H), 1.38 (t, 3H).

2-[4-(3,5-Diethoxyphenyl)phenyl]propionic acid (8)

The hydrolysis of 8b followed the procedure described in the preparation of compound 2. Purification by flash chromatography (30% EtOAc/hexanes+2% AcOH) provided 68 mg of the title compound.

$^1$H NMR (acetone $d_6$) δ 7.60 (d, 2H), 7.42 (d, 2H), 6.75 (d, 2H), 6.45 (t, 1H), 4.10 (m, 4H), 3.80 (m, 1H), 1.48 (d, 3H), 1.38 (t, 3H). MS (FAB+) m/z 359 (M+Na), 269.

EXAMPLE 3

2-[4-(3-(THIOETHYL)PHENYL)PHENYL]PROPANOIC ACID (9)

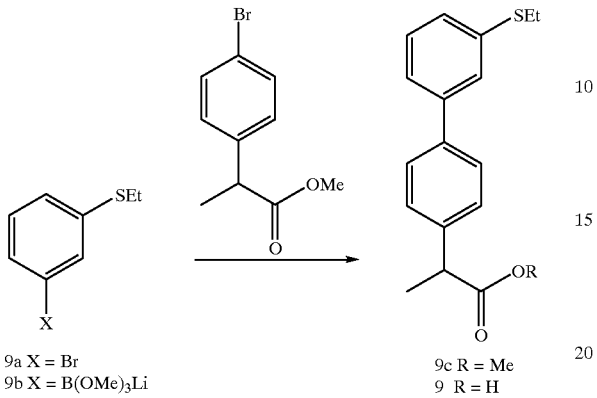

9a X = Br
9b X = B(OMe)₃Li

9c R = Me
9  R = H

1-Bromo-3-(thioethyl)benzene (9a)

To a solution of 3-bromothiophenol (3.0 g, 15.9 mmol) in DMF (40 mL) was added 10N KOH (1.75 mL, 17.4 mmol) followed 15 min later, by iodoethane (2.5 mL, 32 mmol). This mixture was stirred 1 h at room temperature and 2 h at 70° C. The product was extracted twice using Et₂O. The combined organic phases were washed with brine and dried over MgSO₄. Purification by flash chromatography (100% hexanes) provided 3.2 g of the title compound as an orange oil.

$^1$H NMR (acetone d₆) δ 7.47 (m, 1H), 7.35–7.22 (m, 3H), 3.02 (q, 2H), 1.30 (t, 3H).

Lithium (3-(thioethyl)phenyl)trimethylborate (9b)

This compound was prepared from 9a following the procedure described for example 2g.

Methyl 2-[4-(3-(thioethyl)phenyl)phenyl]propanoate (9c)

This compound was prepared from 9b following the procedure described for example 2 h. Purification by flash chromatography (15% EtOAc/hexanes) provided 373 mg of the title compound.

$^1$H NMR (acetone d₆) δ 7.62 (d, 2H), 7.56 (m, 1H), 7.45 (m, 1H), 7.40 (m, 3H), 7.32 (m, 1H), 3.85 (q, 1H), 3.63 (s, 3H), 3.05 (q, 2H), 1.48 (d, 3H), 1.32 (t, 3H).

2-[4-(3-(Thioethyl)phenyl)phenyl]propanoic acid (9)

The hydrolysis of 9c followed the procedure described in the preparation of compound 2. Purification by flash chromatography (30% EtOAc/hexanes+2% AcOH) provided 346 mg of the title compound.

$^1$H NMR (acetone d₆) δ 7.60 (d, 2H), 7.56 (m, 1H), 7.43 (m, 4H), 7.32 (m, 1H), 3.82 (q, 1H), 3.05 (q, 2H), 1.48 (d, 3H), 1.32 (t, 3H). MS (FAB+): 331 (M+Na), 309. Anal. Calc. for C₁₇H₁₇O₂SNa: C, 66.21; H, 5.56; S, 10.40. Found: C, 65.26; H, 5.59; S, 10.41.

EXAMPLE 4

2-[4-(3-((E)-1-PROPENYL)PHENYL)PHENYL]PROPANOIC ACID (12)

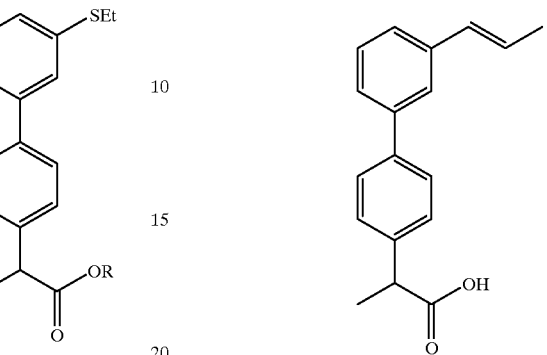

12

This compound was prepared from 10c by the method described for the preparation of compound 10 using EtMgBr instead of MeMgBr, and was isolated as a 1:1 mixture of olefin isomers.

$^1$H NMR (acetone-d₆) δ 7.05–7.61 (8H, m), 6.30–6.55 (2H, m), 3.80 (1H, q), 1.47 & 1.87 (3H, d).

EXAMPLE 5

2-[4-(5-((E)-1-PROPENYL)-3-PYRIDYL)PHENYL]PROPANOIC ACID (14)

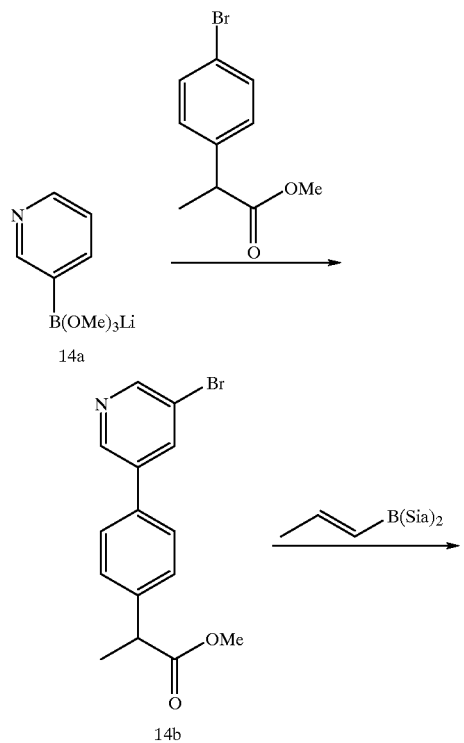

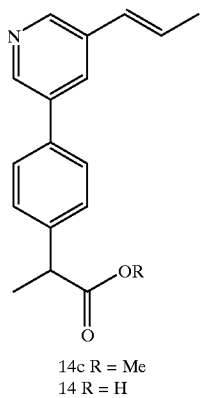

14c R = Me
14 R = H

Lithium (3-bromo-5-pyridyl)trimehthylborate (14a)

To a −100° C. suspension of 3,5-dibromopyridine (5.68 g, 24 mmol) in THF (30 mL) and ether (100 mL) was added nBuLi (1.6 M in hexanes, 15 mL, 24 mmol), giving a yellow suspension. After 15 min, (iPrO)$_3$B (7.5 mL, 32 mmol) was added slowly. The mixture was allowed to warm to 0° C., then was quenched with MeOH and concentrated. The residue was evaporated twice from MeOH to provide 9.4 g of the title compound which was used without further purification.

$^1$H NMR (d$_4$-MeOH) δ 8.48 (m, 1H), 8.26 (m, 1H), 8.00 (m, 1H).

Methyl 2-[4-(5-bromo-3-pyridyl)phenyl]propanoate (14b)

A degassed solution of methyl 2-(4-bromophenyl)propanoate (3.0 g, 12.3 mmol), 14a (total crude material, ~24 mmol), Pd$_2$(dba)$_3$ (240 mg, 0.26 mmol) and triphenylphosphine (260 mg, 1.0 mmol) in toluene (80 mL), nPrOH (25 mL) and water (25 mL) was heated to reflux for 4 h. Cooled and extracted with EtOAc. Washed with saturated aqueous NaHCO$_3$ and brine, and dried over MgSO$_4$. Purification by flash chromatography (20% EtOAc/hexanes) provided 100 mg of the title compound.

$^1$H NMR (d$_6$-acetone) δ 8.84 (m, 1H), 8.64 (m, 1H), 8.24 (m, 1H), 7.72 (m, 2H), 7.46 (m, 2H), 3.87 (q, 1H), 3.65 (s, 3H), 1.49, (d, 3H).

Methyl 2-[4-(5-((E)-1-propenyl)-3-pyridyl)phenyl]propanoate (14c)

To a 0° C. solution of 2-methyl-2-butene (2M in THF, 14 mL, 28 mmol) in THF (20 mL) was added BH$_3$.DMS (10 M in DMS, 1.4 mL, 14 mmol). After 30 min, the solution was allowed to warm to room temperature for 1 h, then cooled to −40° C. A stream of propyne (large excess) was passed through the solution, and the solution was allowed to warm to 0° C., then concentrated. 14b (100 mg, 0.31 mmol), Pd$_2$(dba)$_3$(14 mg, 0.014 mmol) and triphenylphosphine (18 mg, 0.068 mmol) were added, and the mixture was dissolved in 20 mL of 3:1:1 toluene:nPrOH:water. Et$_2$NH (0.5 mL, 4.8 mmol) was added, the solution was degassed, and heated to reflux for 3 h. The mixture was cooled and partitioned between EtOAc and saturated aqueous NH$_4$Cl. The organic phase was washed with brine, dried over MgSO$_4$ and evaporated. Purification by flash chromatography (20% EtOAc/hexanes to 40% EtOAc/hexanes) provided 38 mg of the title compound.

$^1$H NMR (d$_6$-acetone) δ 8.68 (m, 1H), 8.54 (m, 1H), 8.01 (m, 1H), 7.68 (m, 2H), 7.45 (m, 2H), 6.5 (m, 2H), 3.85 (q, 1H), 3.64 (s, 3H), 1.90 (m, 3H), 1.48 (d, 3H).

2-[4-(5-((E)-1-Propenyl)-3-pyridyl)phenyl]propanoic acid (14)

To a solution of 14c (38 mg, 0.13 mmol) in methanol (3 mL) was added 2N NaOH (0.1 mL, 0.2 mmol). The light yellow solution was stirred overnight, then concentrated. The residue was partitioned between pH 7 phosphate buffer and EtOAc. The organic phase was washed with brine, dried over MgSO$_4$ and evaporated to provide 31 mg of the title compound as an oil.

$^1$H NMR (d$_6$-acetone) δ 8.68 (m, 1H), 8.53 (m, 1H), 8.02 (m, 1H), 7.68 (m, 2H), 7.48 (m, 2H), 6.54 (m, 2H), 3.84 (q, 1H), 3.64 (s, 3H), 1.91 (m, 3H), 1.49 (d, 3H). HRMS for 290.11573 (M+1), found 290.11576.

EXAMPLE 6

2-[4-(2-METHYL-1H-5-INDOLYL)PHENYL]PROPANOIC ACID (16)

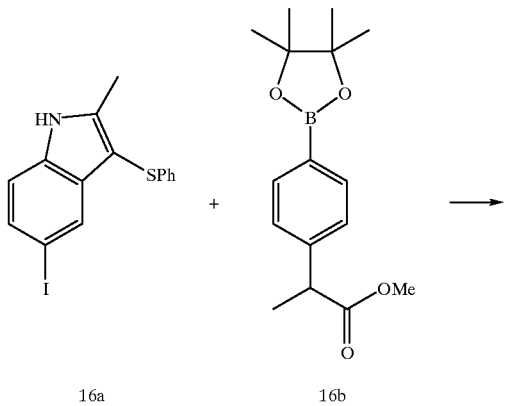

16a        16b

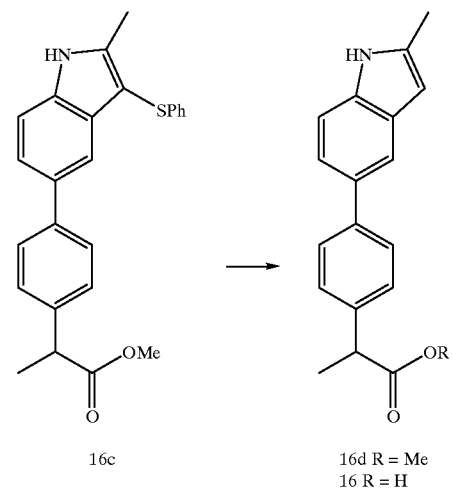

16c        16d R = Me
           16 R = H

5-Iodo-2-methyl-3-(phenylthio)-1H-indole (16a)

To a −60° C. solution of 4-iodoaniline (2.06 g, 9.4 inmol) in CH$_2$Cl$_2$ (50 mL) was slowly added t-butyl hypochlorite (1.4 mL, 12.4 mmol) over 2 min, and the resulting mixture was stirred for an additional 10 min. A solution of 1-(phenylthio)acetone (2.17 g, 13.0 mmol) in CH$_2$Cl$_2$ (3 mL) was added over 3 min and the reaction was allowed to proceed at −60° C. for 1 hour. Et$_3$N (1.85 mL, 13.3 mmol) was slowly added and the reaction was allowed to proceed at room temperature for another hour. The reaction mixture was diluted with water and the layers were separated. The organic layer was dried over MgSO$_4$ and concentrated. The crude product was purified twice by flash chromatography (20 to 30% EtOAc/hexanes) to give 203 mg of a yellow gum.

TLC: R$_f$ 0.4 (30% EtOAc/hexanes). $^1$H NMR (d$_6$-acetone) δ 2.52 (3H, s), 7.01 (3H, m), 7.17 (2H, m), 7.27 (1H, d), 7.38 (1H, dd), 7.75 (1H, d).

Methyl 2-{4-8 2-methyl-3-(phenylthio)-1H-5-indolyl]phenyl}propanoate (16c)

A suspension of diboron dipinacolate (205 mg, 0.81 mmol), [1,2-bis(diphenylphosphino)-ethane]dichloropalladium(II) (27 mg, 47 μmol) and KOAc (217 mg, 2.2 mmol) in DMSO (2 mL) was degassed by bubbling $N_2$ for 10 min. Then methyl 2-(4-bromophenyl)propanoate (112 μL, 0.6 mmol) was added and the resulting mixture was heated at 85° C. for 2 hours and allowed to cool to room temperature. To this mixture was added a 2.0M aqueous solution of $Na_2CO_3$ (1.5 mL, 3 mmol) and a solution of 16a (203 mg, 0.55 mmol) in DMSO (2 mL). The mixture was degassed by bubbling with $N_2$ for 10 min., [1,1'-bis(diphenylphosphino) ferrocene]-dichloropalladium(II).$CH_2Cl_2$ (19 mg, 23 μmol) was added and the reaction was heated at 85° C. for 2 hours. Then another portion of palladium catalyst was added (12 mg, 15 μmol) and the reaction was heated for another 2 hours. The reaction was allowed to cool to room temperature, diluted with EtOAc, washed with water, dried over $MgSO_4$ and concentrated. The crude product was purified by flash chromatography (15 to 20% EtOAc/hexanes) to give 37 mg of the title compound as a yellow gum.

$^1$H NMR ($d_6$-acetone) δ 1.45 (3H, d), 2.55 (3H, s), 3.62 (3H, s), 3.78 (1H, q), 7.04 (3H, m), 7.17 (2H, m), 7.34 (2H, d), 7.48 (2H, m), 7.58 (2H, d), 7.67 (1H, s), 10.7 (1H, b).

Methyl 2-[4-(2-methyl-1H-5-indolyl)phenyl]propanoate (16d)

A mixture of 10c (37 mg, 90 μmol), thiosalicylic acid (31 mg, 200 μmol) and TFA (1 mL) was heated to 70° C. for 10 min. The TFA was removed under reduced pressure and the resulting residue was purified by flash chromatography (15% EtOAc/hexanes) to provide 24 mg of the title compound as a colorless gum.

$^1$H NMR ($d_6$-acetone) δ 1.48 (3H, d), 2.44 (3H, s), 3.64 (3H, s), 3.81 (1H, q), 6.21 (1H, s), 7.35 (4H, m), 7.62 (1H, d), 7.70 (1H, s), 10.0 (1H, b).

2-[4-(2-methyl-1H-5-indolyl)phenyl]propanoic acid (16)

To a solution of 16d (24 mg, 82 μmol) in THF (2 mL) and MeOH (0.5 mL) was added a 1.0N aqueous solution of LiOH (0.2 mL, 200 μmol) and the resulting mixture was stirred at room temperature overnight. The reaction was diluted with a 25% aqueous solution of $NH_4OAc$ and extracted with EtOAc. The organic layer was dried over $MgSO_4$ and concentrated. Purification by flash chromatography (30:70:1 EtOAc/hexane/AcOH) gave 23 mg of the title compound as a light yellow gum.

$^1$H NMR ($d_6$-acetone) δ 1.48 (3H, d), 2.43 (3H, s), 3.78 (1H, q), 6.21 (1H, s), 7.33 (2H, m), 7.40 (2H, d), 7.62 (2H, d), 7.69 (1H, s), 10.0 (1H, b). MS (APCI, neg. ion) 278 (M−1), 234.

Biological activity of the compounds of formula I is demonstrated using the assays described below.

Purified-enzyme COX1 and COX2 assays

Recombinant human COX-2 was expressed and purified as previously described (Cromlish et al. Arch. Biophys. Biochem. 1994 314, 193–199; Percival et al. Arch. Biophys. Biochem. 1994 315, 111–118). Recombinant human COX-1 was expressed (Cromlish and Kennedy, Biochem. Pharmacol. 1996 52, 1777–1785) and purified as described for COX-2 except that the protein was solubilised in 1.5% w/v decylmaltoside and ion exchange chromatography was performed in the presence of 0.2% w/v decylmaltoside. COX activity in the presence of inhibitors was determined by the method described in Riendeau et al. (*Brit. J. Pham.* 1997 121, 105–117) with minor modifications. The assay mixture contained 2 mM genapol X-100 and in the case of COX-1 10 μM N,N,N',N'-tetramethyl-p-phenylenediamine in addition to the components mentioned in the above reference. COX-1 and COX-2 $IC_{50}$ values were determined and a ratio of COX-1 $IC_{50}$/COX-2 $IC_{50}$ was calculated to determine selectivity for the compounds of COX-2 over COX-1.

The compounds of the examples have a ratio of COX-1 $IC_{50}$/COX-2 $IC_{50}$ in the range of approximately 9 to approximately 100, which demonstrates a high level of selectivity for COX-2 in the compounds of the invention. In comparison, flurbiprofen has a COX-1 $IC_{50}$/COX-2 $IC_{50}$ ratio of approximately 1.1, indicating that it is not COX-2 selective.

Flurbiprofen has the following structural formula:

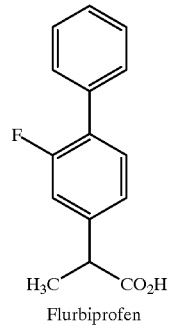

Flurbiprofen

While certain preferred embodiments are described herein in detail, numerous alternative embodiments are contemplated as falling within the scope of the invention. Consequently, the invention is not limited to the specific embodiments disclosed herein.

What is claimed is:

1. A compound represented by formula I:

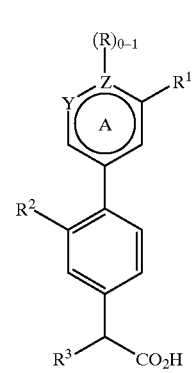

or a pharmaceutically acceptable salt, ester or tautomer thereof, wherein:

Z is C

R represents H and $R^1$ is a moiety which has the following characteristics:
(a) it is a linear chain of 3-4 atoms containing 0–2 double bonds, which can adopt an energetically stable transoid configuration and if a double bond is present, the bond is in the trans configuration;
(b) it is lipophilic except for the atom bonded directly to ring A, which is either lipophilic or non-lipophilic; and
(c) there exists an energetically stable configuration planar with ring A to within about 15 degrees, or R and $R^1$ are taken in combination and represent a 5- or 6-membered aromatic or non-aromatic ring B fused to ring A, said ring B containing 0–3 heteroatoms selected from O, S and N, said ring B being lipophilic except for the atoms attached directly to ring A, which are lipophilic or non-lipophilic, and said ring B having available an energetically stable configuration planar with ring A to within about 15 degrees;

said ring B further being substituted with 1 $R^a$ group selected from the group consisting of: $C_{1-2}$ alkyl, —$OC_{1-2}$ alkyl, —$NHC_{1-2}$ alkyl, —$N(C_{1-2}$ alkyl$)_2$, —$C(O)C_{1-2}$ alkyl, —S—$C_{1-2}$ alkyl and —$C(S)C_{1-2}$ alkyl;

Y represents CH or C—$OC_{1-3}$ alkyl;

$R^2$ represents H, Br, Cl or F, and $R^3$ represents H or $CH_3$.

2. A compound represented by formula I:

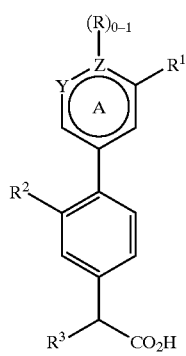

or a pharmaceutically acceptable salt, ester or tautomer thereof, wherein:

Z is C;

R represents H and $R^1$ represents a member selected from the group consisting of:

—$C_{3-4}$ alkenyl, —$C_{3-4}$ alkynyl, —X—$C_{2-3}$ alkynyl, —X—$C_{2-3}$ alkyl and —X—$C_{2-3}$ alkenyl, wherein X represents O, S or NH;

or R and $R^1$ are taken in combination and together represent a 5- or 6-membered aromatic or non-aromatic ring B fused lo ring A containing 0–3 heteroatoms selected from O, S and N;

said ring B further being substituted with 1 $R^a$ group selected from the group consisting of: $C_{1-2}$ alkyl, —$OC_{1-2}$ alkyl, —$NHC_{1-2}$ alkyl, —$N(C_{1-2}$ alkyl$)_2$, —$C(O)C_{1-2}$ alkyl, —S—$C_{1-2}$ alkyl and —$C(S)C_{1-2}$ alkyl;

Y represents CH or C—$OC_{1-3}$ alkyl;

$R^2$ represents H, Br, Cl or F, and $R^3$ represents H or $CH_3$.

3. A compound in accordance with claim 2 wherein R represents H and $R^1$ represents a member selected from the group consisting of:

—X-ethyl, —X-propyl, —X-vinyl, —X—CH=CHCH$_3$, —X—CH$_2$CH=CH$_2$, —CH=CHCH=CH$_2$, —C≡CCH$_3$ and —C≡CCH$_2$CH$_3$, wherein X represents O, S or NH.

4. A compound in accordance with claim 2 wherein:

R and $R^1$ are taken in combination and together represent a 5- or 6-membered aromatic or non-aromatic ring B fused to ring A of the formula:

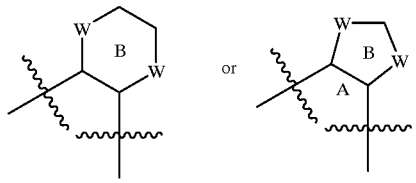

wherein each W independently represents C, O, S or N;

said ring B further being substituted with 1 $R^a$ group selected from the group consisting of: $C_{1-2}$ alkyl, —$OC_{1-2}$ alkyl, —$NHC_{1-2}$ alkyl, —$N(C_{1-2}$ alkyl$)_2$, —$C(O)C_{1-2}$ alkyl, —S—$C_{1-2}$ alkyl and —$C(S)C_{1-2}$ alkyl;

Y represents CH or C—$OC_{1-3}$ alkyl, and $R^2$ represents H, Br, Cl or F.

5. A compound in accordance with claim 1 represented by one of the following structural formulas:

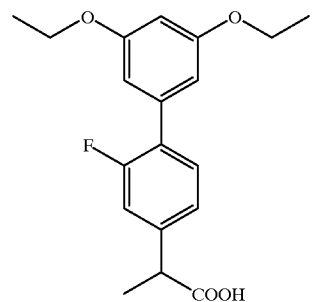

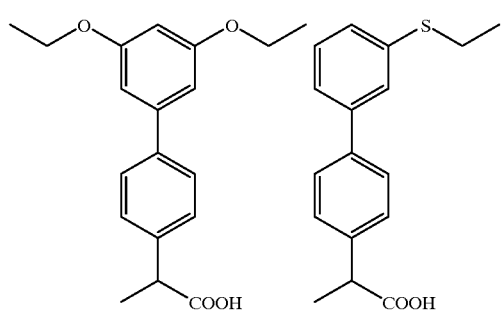

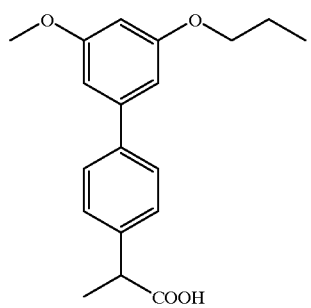

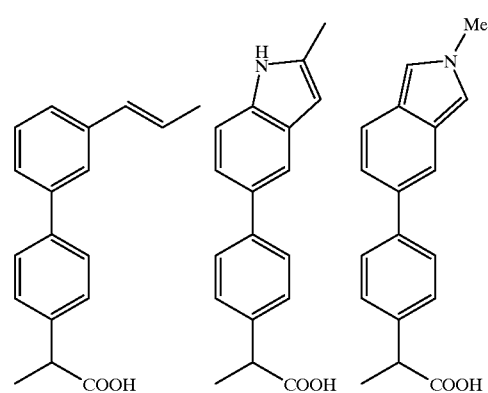
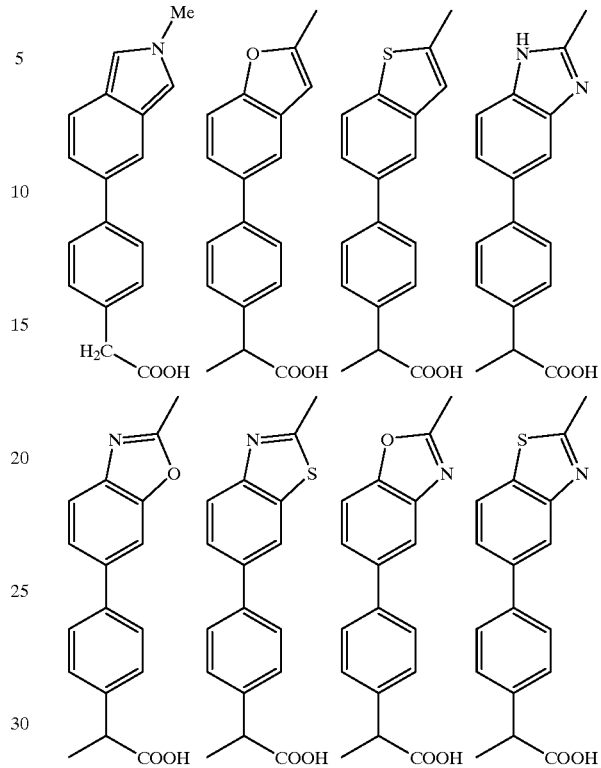
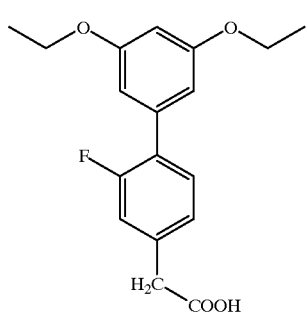
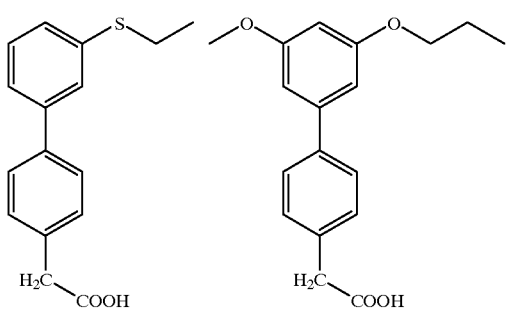
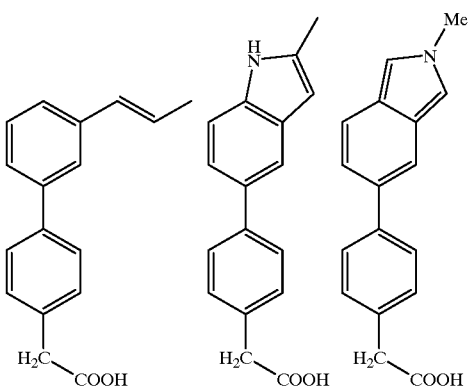

or a salt, ester of the carboxyl acid moiety or tantomer thereof.

6. A compound in accordance with claim 2 wherein: Y represents CH or C—OC$_{1-3}$ alkyl.

7. A compound in accordance with claim 2 wherein R$^2$ represents H or F.

8. A compound in accordance with claim 2 wherein R$^3$ represents CH$_3$.

9. A compound in accordance with claim 2 in the form of a salt.

10. A compound in accordance with claim 8 wherein the salt is a sodium, potassium, calcium or magnesium salt.

11. A compound in accordance with claim 1 represented by one of the following structural formulas:

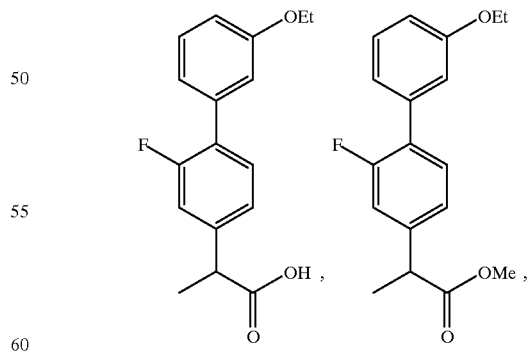

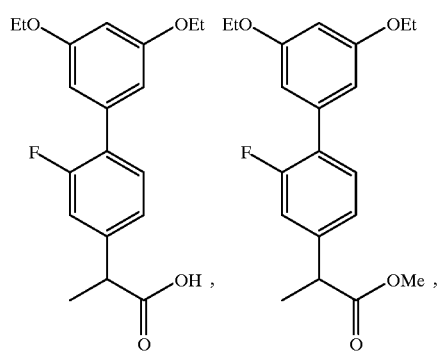

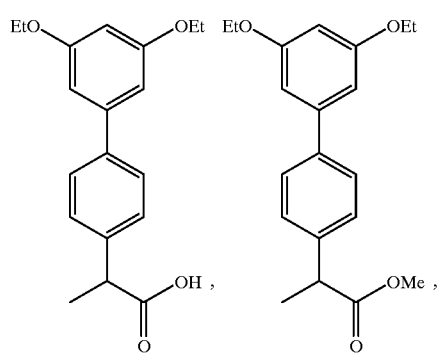

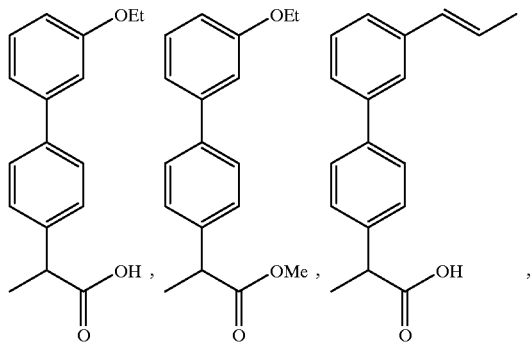

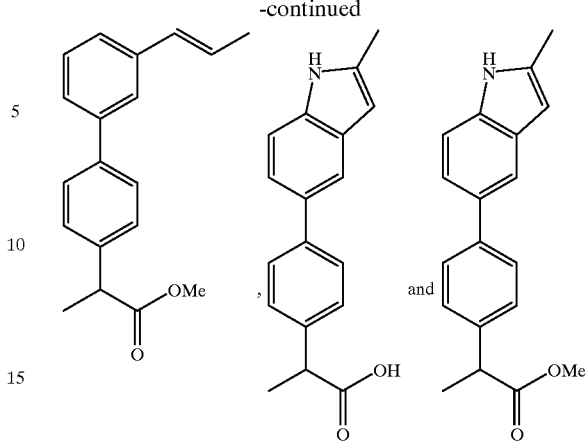

12. A pharmaceutical composition which is comprised of a compound in accordance with claim 1 in combination with a pharmaceutically acceptable carrier.

13. A method of treating a COX-2 mediated disease or condition in a mammalian patient in need of such treatment, comprising administering to said patient a compound in accordance with claim 1 in an amount which is effective to treat a COX-2 mediated disease or condition.

14. A method of treating a COX-2 mediated disease or condition in accordance with claim 13 wherein the COX-2 mediated disease or condition is selected from the group consisting of:

rheumatic fever, symptoms associated with influenza or other viral infection, common cold, low back pain, neck pain, dysmenorrhea, headache, migraine, toothache, sprain, strain, myositis, neuralgia, synovitis, arthritis, rheumatoid arthritis, degenerative joint disease, osteoarthritis, gout, ankylosing spondylitis, bursitis, burns, post-operative pain, cellular neoplastic transformations, metastatic tumour growth, diabetic retinopathy, tumour angiogenesis, autoimmune disease, type I diabetes, type II diabetes, lupus erythematosus, Graves' disease, irritable bowel syndrome, Crohn's disease, prostanoid-induced smooth muscle contraction, premature labour, asthma, eosinophil related disorders, Alzheimer's disease, bone loss (osteoporosis) and glaucoma.

15. A method of treating a COX-2 mediated disease or condition in accordance with claim 14 wherein the disease or condition is arthritis.

16. A method of treating a COX-2 mediated disease or condition in accordance with claim 14 wherein the disease or condition is diabetes.

* * * * *